US012745807B2

(12) United States Patent
Kiyonaga et al.

(10) Patent No.: US 12,745,807 B2
(45) Date of Patent: Sep. 29, 2026

(54) PASSIVE, MULTIPLE SENSATION INHALATION DEVICE

(71) Applicant: Past Patterns, LLC, Santa Barbara, CA (US)

(72) Inventors: Davis Kiyonaga, Santa Barbara, CA (US); Evan Abel, Rockaway Park, NY (US)

(73) Assignee: Past Patterns, LLC, Santa Barbara, CA (US)

( * ) Notice: Subject to any disclaimer, the term of this patent is extended or adjusted under 35 U.S.C. 154(b) by 0 days.

(21) Appl. No.: 19/390,978

(22) Filed: Nov. 17, 2025

(65) Prior Publication Data

US 2026/0150912 A1 Jun. 4, 2026

Related U.S. Application Data

(60) Provisional application No. 63/727,858, filed on Dec. 4, 2024.

(51) Int. Cl.
*A24F 42/20* (2020.01)
*A24F 42/60* (2020.01)
*A61M 15/06* (2006.01)

(52) U.S. Cl.
CPC .............. *A24F 42/20* (2020.01); *A24F 42/60* (2020.01); *A61M 15/06* (2013.01)

(58) Field of Classification Search
CPC .......... A24F 42/20; A24F 42/60; A24F 40/05; A24F 40/10; A24F 40/42; A24F 47/00; A24D 1/20; A61M 15/00; A61M 15/0001; A61M 15/0021; A61M 15/02; A61M 15/06; A61M 11/00; A61M 11/04
See application file for complete search history.

(56) References Cited

U.S. PATENT DOCUMENTS

| | | | | | |
|---|---|---|---|---|---|
| 4,284,089 | A * | 8/1981 | Ray | A24F 42/60 | 131/270 |
| 4,774,971 | A * | 10/1988 | Vieten | A24F 42/20 | 131/362 |
| 4,917,120 | A * | 4/1990 | Hill | A24B 15/16 | 131/273 |
| 5,799,663 | A * | 9/1998 | Gross | A24F 42/60 | 131/273 |
| 2002/0179101 | A1* | 12/2002 | Chavez | A61M 15/06 | 131/273 |
| 2008/0000487 | A1* | 1/2008 | Valadi | A24D 3/17 | 131/273 |
| 2020/0035121 | A1* | 1/2020 | Pandolfino | A24B 15/167 | |
| 2021/0244076 | A1* | 8/2021 | Ferrie | A24B 15/302 | |
| 2024/0389679 | A1* | 11/2024 | Black | A24D 3/04 | |

* cited by examiner

*Primary Examiner* — Joseph D. Boecker
(74) *Attorney, Agent, or Firm* — Armon Shahdadi; Pierson Ferdinand LLP

(57) ABSTRACT

A method and device for providing a multiple-sensation inhalation experience are described. The method involves machining a bamboo tube to create a hollow cavity with an inlet and outlet, soaking the tube in a flavor solution, and inserting a cotton insert soaked in a sensation solution. A second cotton insert can also be inserted to control and customize air flow through the device. The device comprises a machined bamboo tube infused with a flavor solution and a cotton insert infused with a sensation solution, allowing users to experience taste and sensation when inhaling through the device.

17 Claims, 7 Drawing Sheets

PASSIVE, MULTIPLE SENSATION INHALATION DEVICE

BACKGROUND

In recent years, there has been a growing interest in alternatives to traditional smoking. For example, electronic cigarettes (i.e., "vapes") have entered the market and provide users with the ability to inhale flavorful vapor that can produce various effects based on the content of the vapor. These vapes typically produce various sensations for the user, such as a taste sensation based on the flavor of the vapor, as well as the sensation of the physical feeling in the throat when inhaling vapor, also known as "throat feel." These sensations can vary based on the content and temperature of the vapor.

As another alternative to traditional smoking, a new market has emerged for entirely smokeless and vaporless products that recreate some aspects of traditional smoking. These products can help some users quit smoking or can provide a pleasant experience without any downsides that may be associated with smoking or vaping. However, the products in this new market suffer from the problem of providing all flavor or sensation through a singular mechanism. For example, some products provide a metal or plastic body portion with a flavored substance inside which, when air is inhaled through the product, imparts the flavor to the air being inhaled. However, regardless of the mix of flavors used for the substance, these products produce only a singular sensation.

There is a demand for products that offer a more holistic and enjoyable experience, combining multiple sensations of taste, aroma, tactile feel, and throat feel from different sources within the product. There is also a demand for products that more accurately reproduce the sensations of vaping. There is a further need for products that forego plastic or metal mouthpieces and instead use more pleasing tactile and flavorful materials.

SUMMARY

Examples described herein include systems and methods for providing a multiple-sensation inhalation device that satisfies the goals and needs laid out above.

In accordance with embodiments, a method is provided for creating a multiple-sensation inhalation device. The method involves machining a permeable material, such as bamboo, into a tube that includes a hollow cavity with an inlet and an outlet. While bamboo is described throughout this disclosure, it should be understood that any other suitable permeable material can be substituted. The machined bamboo tube is then soaked in a flavor solution to allow the flavor to penetrate the bamboo. A cotton insert, designed to fit within the inlet of the bamboo tube and allowing for airflow, either by way of one or more apertures or by using material with a low enough density to allow for flow through the material, is soaked in a sensation solution containing at least one essential oil or extract. The cotton insert is then placed into the inlet of the bamboo tube. While cotton is described throughout this disclosure for the inserts within the device, any other suitable material may be used. For example, any material that can absorb a sensation solution while also sufficiently retaining its shape for insertion into the device can be used.

As used herein, the word "sensation" is intended to encompass any physical feeling or perception. A sensation can be localized, such as a numbing or cooling feeling in the throat, or can be more generalized in the body, such as when nicotine enters the bloodstream.

In some examples, a second cotton insert is placed into the inlet of the bamboo tube alongside the first cotton insert. In those examples, the first cotton insert is soaked in the sensation solution while the second cotton insert is not. This can allow for the different cotton inserts to perform different functions and be independently replaceable. In some embodiments, the cotton insert is capable of retaining the sensation solution, ensuring that the user experiences the intended sensation when inhaling through the cotton insert. The second cotton insert can manage airflow in various ways, such as by providing a density of cotton that allows air to flow through a solid insert, or alternatively by including one or more apertures to manage airflow. These apertures can be arranged in a specific pattern, such as a central aperture surrounded by multiple other apertures. In some examples, a product can include multiple second cotton inserts that provide different levels of airflow, such that a user can select from multiple options and customize the device to their own preferences.

Regardless of how many cotton inserts are used, they can be provided in a manner that allows a user to replace them as desired. In one example, a user can select between different inserts that provide different levels of airflow resistance. This can allow the user to test different configurations to find what suits them, or even change configurations as the product ages and flavors become less intense over time. In some examples, a user can choose between inserts soaked in different sensation solutions, allowing the user to test different sensations and customize the product to their liking.

In some examples, the flavor solution used in the method for the bamboo tube may include flavors such as bubble gum, fruit, tiramisu, or chocolate. This allows for a variety of taste experiences when using the inhalation device. The machined bamboo tube is designed to retain the flavor solution, enabling the user to experience a taste when inhaling through the tube, particularly when the user's lips contact the outer surface of the bamboo tube. In an example, the sensation solution for soaking the cotton insert may include ingredients like peppermint, menthol, lavender, vitamin B12, caffeine, nicotine, THC, CBD, or betel nut. These ingredients provide different sensory experiences during inhalation. For example, the flavor solution can provide a flavor based on a user's lips contacting the bamboo tube, while the sensation solution provides a throat feel as the user inhales through the device.

Although examples herein describe the entire machined tube being made from bamboo or another permeable material, in some examples only the mouthpiece of the device is made from the permeable material while the remainder of the tube is another material. In yet another embodiment, both the mouthpiece and the remainder of the tube are made from a permeable material but can be separated from one another, allowing for soaking of the mouthpiece in flavor solution while the remainder of the tube is not soaked in any solution. The common thread in these examples is that the portion of the device intended to contact a user's lips is soaked in a flavor solution, thereby providing the flavor experience. This can be paired with the throat feel from the sensation solution, as described. It is understood that this description encompasses all of these variations.

Both the foregoing general description and the following detailed description are exemplary and explanatory only and are not restrictive of the examples, as claimed.

DETAILED DESCRIPTION

Reference will now be made in detail to the present examples, including examples illustrated in the accompanying drawings.

A method and device for providing a multiple-sensation inhalation experience are described. The method involves machining a bamboo tube to create a hollow cavity with an inlet and outlet, soaking the tube in a flavor solution, and inserting a cotton insert soaked in a sensation solution. A second cotton insert can also be inserted to control and customize air flow through the device. The device comprises a machined bamboo tube infused with a flavor solution and a cotton insert infused with a sensation solution, allowing users to experience taste and sensation when inhaling through the device.

Figure 1:
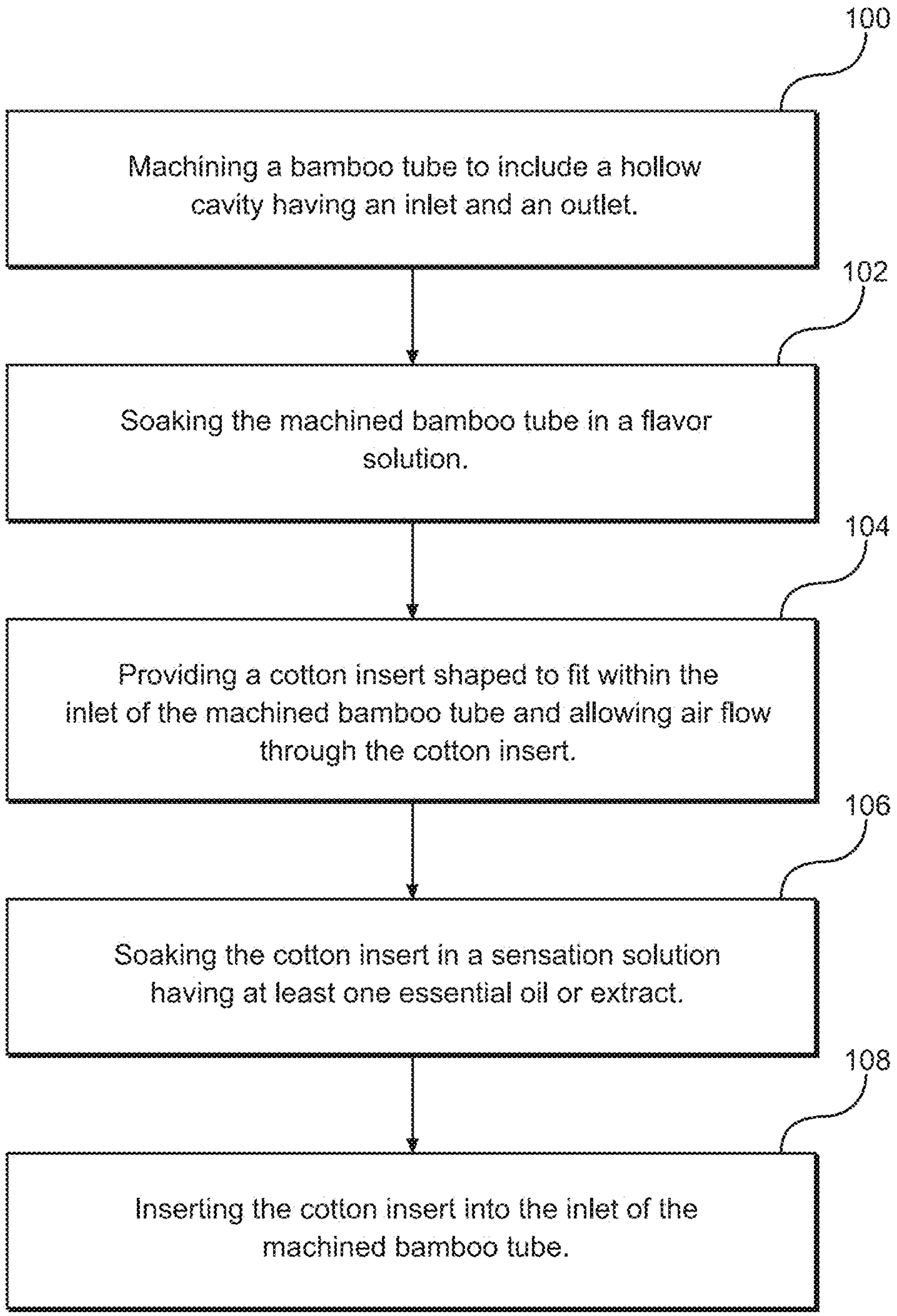
FIG. 1 is a flowchart of an example method for providing a passive, multiple-sensation inhalation device.

FIG. 1 is a flowchart illustrating a method for providing a multiple-sensation inhalation device, according to an example embodiment. At stage 100 of the method, a bamboo tube may be machined to include a hollow cavity with an inlet and an outlet. This machining process creates a structure that facilitates airflow through the bamboo tube and retains the necessary components. The machining process can include starting with a bamboo block that is machined into a tube. This machined bamboo tube can function as a mouthpiece in some examples, or it can be used for the entire tube. In examples where the machined bamboo tube is a mouthpiece, the remainder of the tube can be made from a different material that need not be permeable. For example, rather than machining a bamboo tube, the tube can be 3D printed from another suitable material, such as stainless steel. Similarly, the mouthpiece portion can be made from a material other than bamboo, provided it can absorb and hold flavor solution. For ease of reference, the tube is referred to as a bamboo tube throughout, but should not be so limited.

At stage 102, the bamboo tube may then be soaked in a flavor solution, infusing the bamboo with flavor. This flavor may be located on the outer surface of the bamboo tube, where it comes into contact with the user's lips during inhalation. The flavor solution may include various flavors such as bubble gum, fruit, tiramisu, chocolate, or any other flavor, enhancing the user's experience by providing a taste sensation. The machined bamboo tube retains the flavor solution, allowing the user to experience the taste when inhaling through the tube. The machined bamboo tube, with its hollow cavity, is designed to allow airflow, which is essential for the inhalation process. The flavor-infused bamboo tube thus plays a role in the overall functionality of the multiple-sensation inhalation device, contributing to the combination of flavor and sensation that the device aims to deliver.

At stage 104, a cotton insert, shaped to fit within the inlet of the machined bamboo tube, may be provided with at least one aperture to allow airflow through the insert. This stage can include providing a single cotton insert in some examples, but may also include two cotton inserts that provide different functions. Either cotton insert may include multiple apertures arranged in a pattern, optimizing airflow and providing the desired amount of air resistance. The pattern may have a central aperture surrounded by multiple apertures, based on the ratio of air to material, manufacturability, and the size of holes. In some examples, the cotton insert does not include any apertures, but instead uses a light density that allows for airflow through the material.

At stage 106, the cotton insert may be soaked in a sensation solution containing essential oils or extracts such as peppermint, menthol, lavender, vitamin B12, caffeine, nicotine, THC, CBD, or betel nut. This soaking process infuses the cotton insert with a sensation, such as a cooling feeling in the throat, that the user experiences when inhaling through the insert. In an example, a first cotton insert is soaked in the sensation solution while a second cotton insert is inserted for purposes of optimizing airflow and air resistance.

At stage 108 of the example method, the cotton insert or inserts are inserted into the inlet of the machined bamboo tube. This assembly allows the user to experience both the flavor and sensation when inhaling through the device, as the flavor on the outer surface of the bamboo tube and the sensation from the cotton insert combine to enhance the inhalation experience and simulate the sensations produced by inhaling from a vape or other traditional smoking device.

Regardless of how many cotton inserts are used, they can be provided in a manner that allows a user to replace them as desired. In one example, a user can select between different inserts that provide different levels of airflow resistance. This can allow the user to test different configurations to find what suits them, or even change configurations as the product ages and flavors become less intense over time. In some examples, a user can choose between inserts soaked in different sensation solutions, allowing the user to test different sensations and customize the product to their liking.

Figure 2:
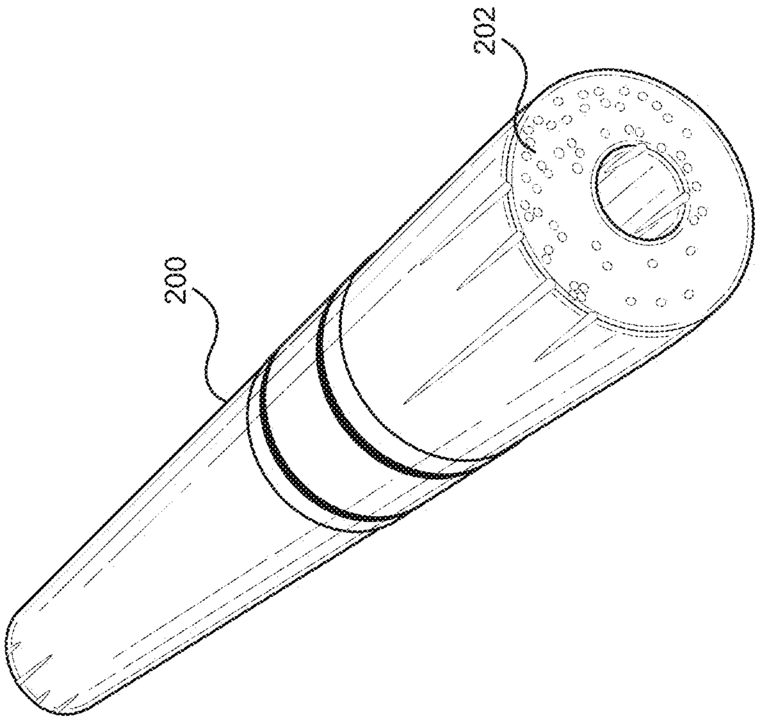
FIG. 2 is a perspective view of an example inhalation device in accordance with embodiments described herein.
Figure 3:
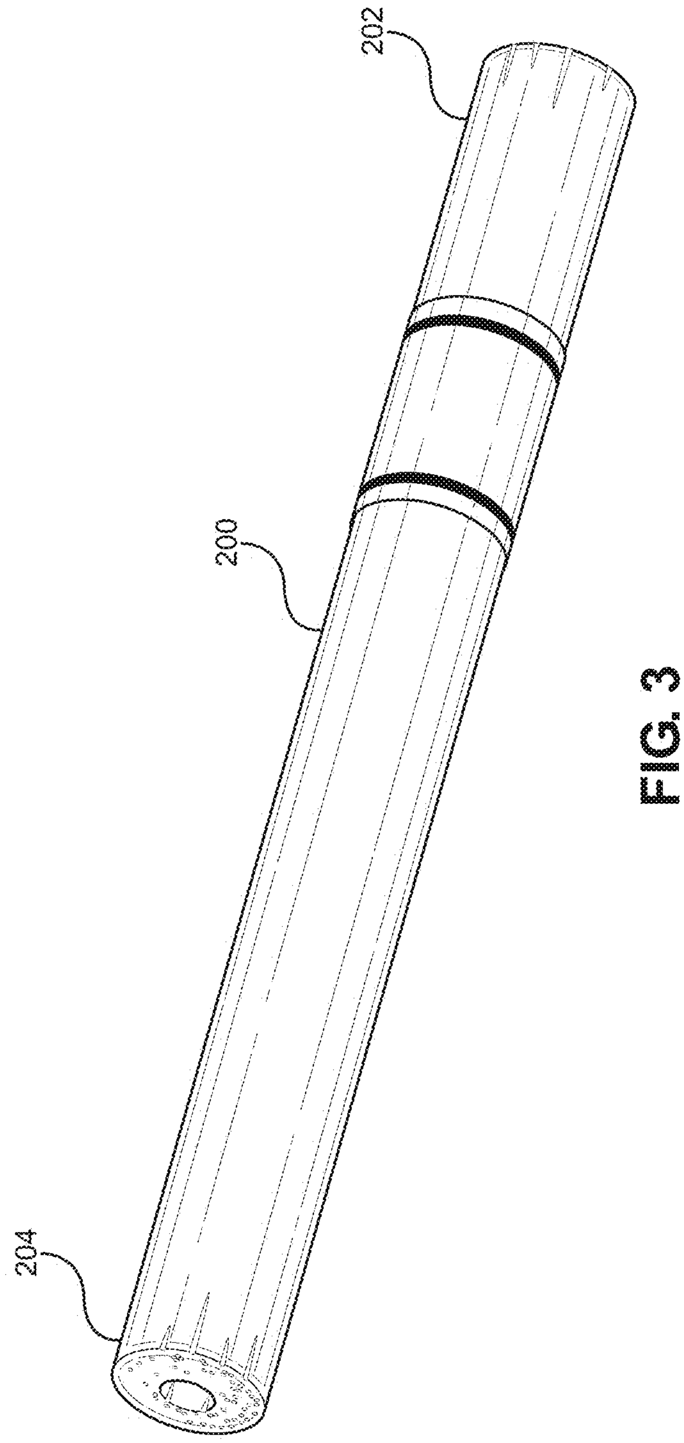
FIG. 3 is a perspective view of an example inhalation device in accordance with embodiments described herein.

FIGS. 2 and 3 show an example assembled inhalation device 200 in accordance with embodiments described herein. The device 200 includes a bamboo tube having an airflow outlet 202 and inlet 204. As explained above, although bamboo is identified as the material used for the tube throughout this disclosure, it should be understood that any other suitable permeable material can be substituted. For example, any material that can become infused with a flavor solution could be used. Similarly, although the embodiment of FIGS. 2 and 3 use bamboo for the entire tube, in other embodiments only the mouthpiece portion of the device is made from bamboo or similar permeable material. The mouthpiece can include the outlet 202 end of the device 200 as shown in the drawings.

Figure 4:
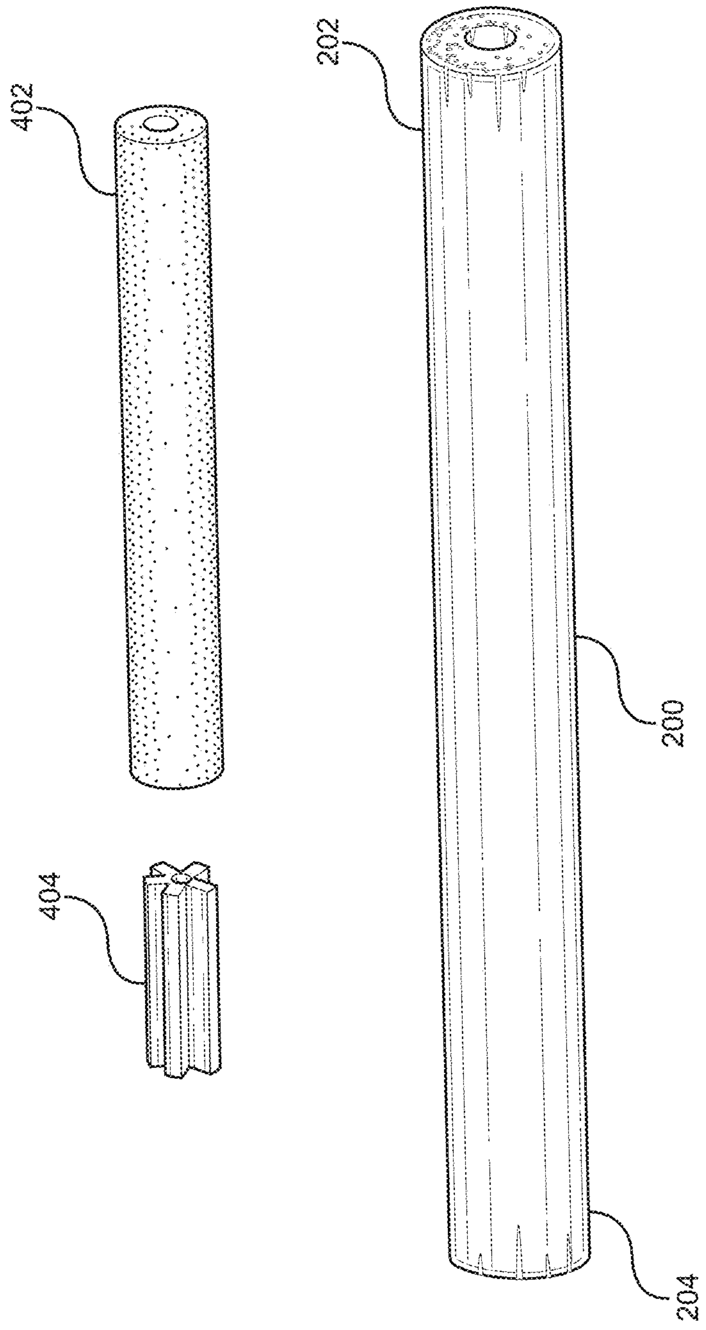
FIG. 4 is a perspective view of a deconstructed example inhalation device in accordance with embodiments described herein.
Figure 5:
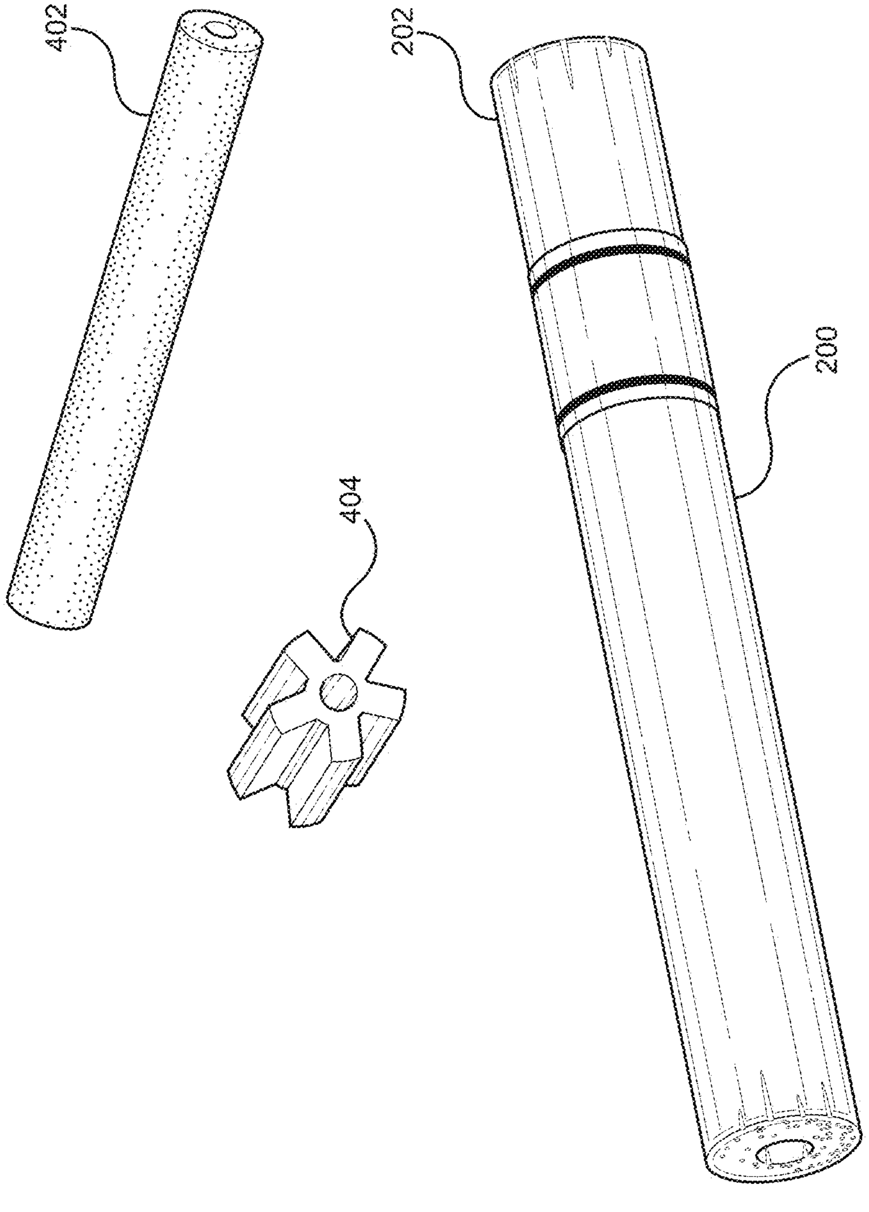
FIG. 5 is a perspective view of a deconstructed example inhalation device in accordance with embodiments described herein.
Figure 6:
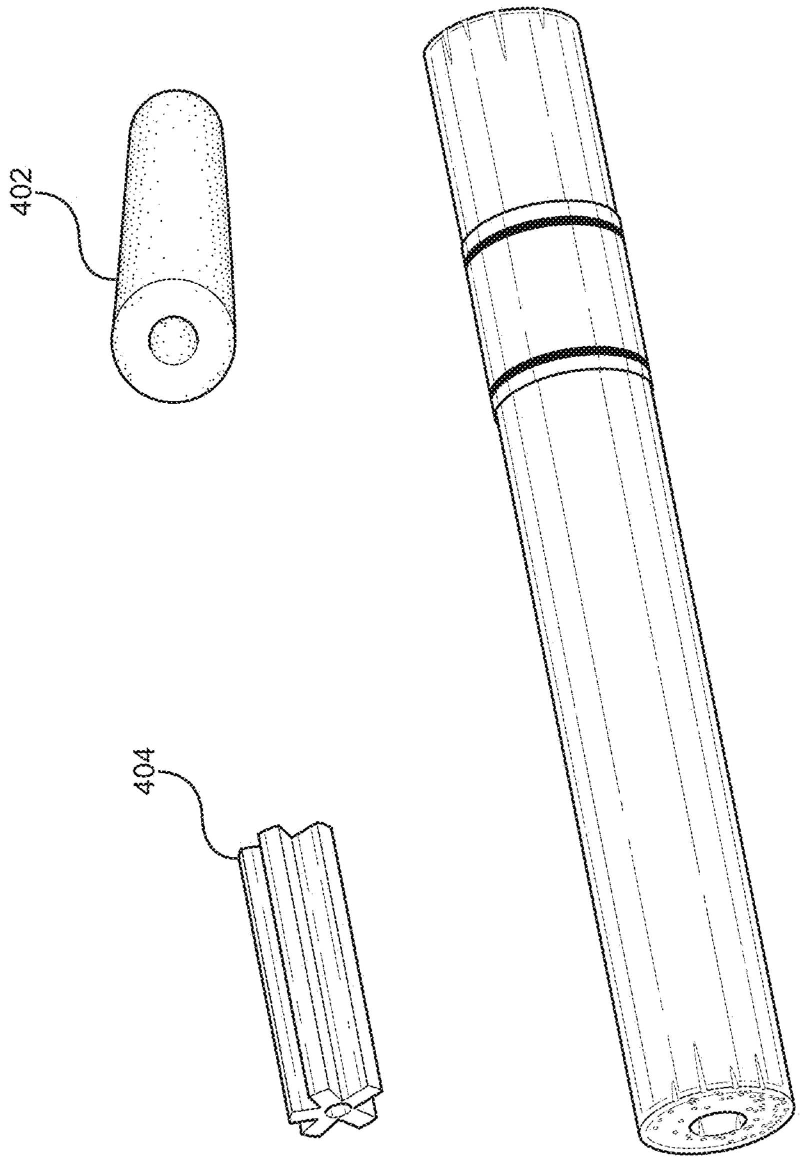
FIG. 6 is a perspective view of a deconstructed example inhalation device in accordance with embodiments described herein.

FIGS. 4-6 show an example of the inhalation device 200 of FIGS. 2 and 3, but with a first cotton insert 402 and second cotton insert 404 removed. In this example, the first cotton insert 402 includes a single aperture through its longitudinal center, although any hole pattern can be utilized. In this embodiment, the first cotton insert 402 has been soaked in a sensation solution that includes at least one essential oil or extract, such as menthol, peppermint, lavender, vitamin B12, caffeine, nicotine, THC, CBD, or betel nut. The size and number of holes through the first cotton insert 402 can dictate how much of the sensation solution is infused into the air that flows through the device 200. Generally speaking, more surface area in contact with the flow of air will result in more sensation solution infusing the air, leading to a stronger sensation.

The embodiment of FIGS. 4-6 also shows a second cotton insert 404. In this embodiment, the second cotton insert 404 is not soaked in the sensation solution but is instead utilized for control of the airflow and flow resistance within the device 200. The second cotton insert 404 can include one or more apertures, including a pattern such as that shown in FIG. 5. The size and pattern of the holes in the second cotton insert 404 can be varied to change the airflow characteristics. The pattern shown in FIG. 5 includes several cutouts that form holes or apertures through the insert once inserted into the tube. In some embodiments, a user can swap different cotton inserts 404 to change the sensation profile of the device 200. As an example, when the product is new, a lower airflow may provide sufficient sensation for the user. But as the product is used and the sensation begins to decline, the user can change swap the cotton insert 404 with a different insert having larger holes or a greater number of holes, providing more airflow that can increase the sensation.

In another embodiment, different portions of a permeable tube can be soaked in different solutions to achieve different effects. For example, the device can include a mouthpiece portion and a tube portion. The mouthpiece portion can be soaked in a flavor solution while the tube portion can be soaked in a sensation solution. In yet another embodiment, the mouthpiece and tube are combined into a single tube, where one end of the tube is soaked in a flavor solution while the other end of the tube is soaked in a sensation solution.

Figure 7:
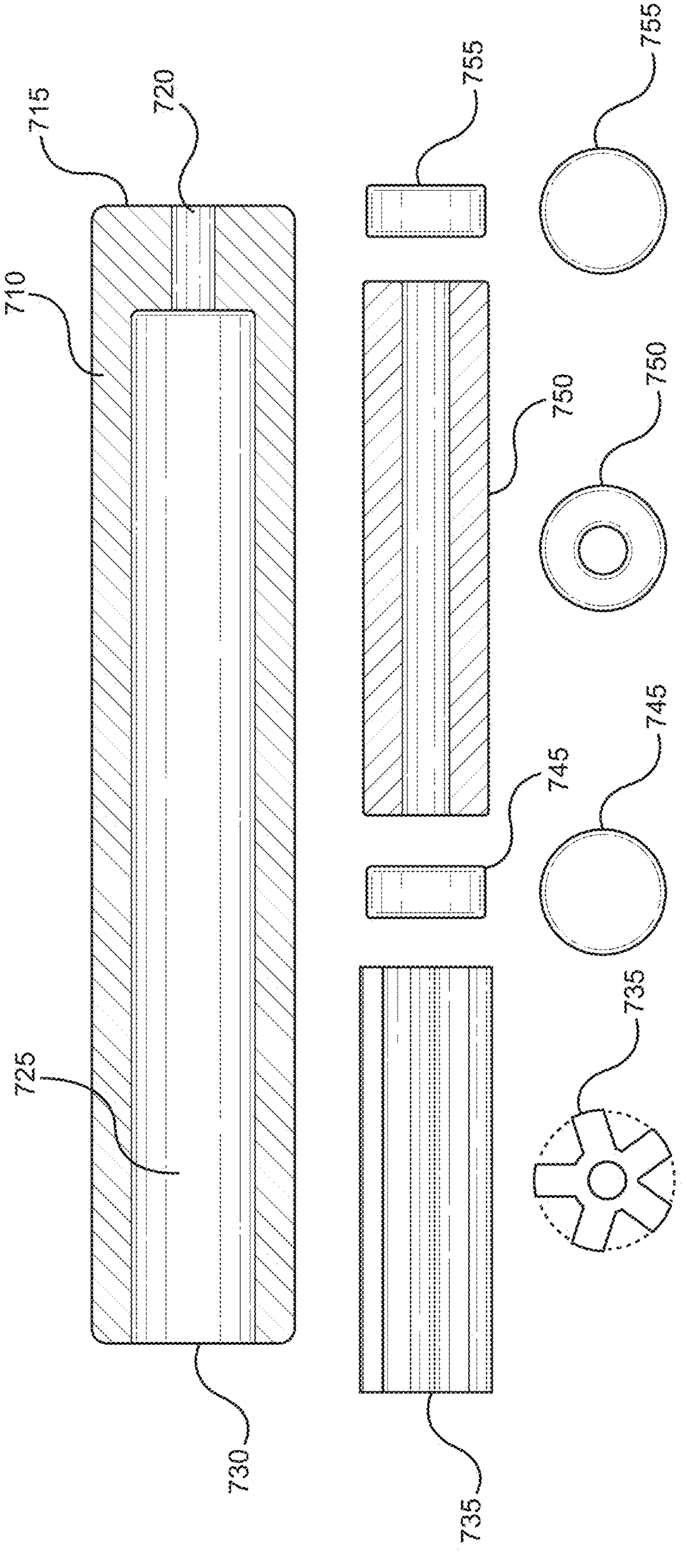
FIG. 7 is a cross-sectional view of a deconstructed example inhalation device with additional components in accordance with embodiments described herein.

FIG. 7 provides a cross-sectional, exploded view of an example inhalation device 710 that demonstrates the modular configuration of internal components designed to fit within an internal cavity 725. The inhalation device 710 can include a mouthpiece 715 positioned at one end and an inlet 730 positioned at the opposite end. An outlet channel 720 may be formed within the mouthpiece 715 to facilitate airflow from the internal cavity 725 to the user's mouth during inhalation.

The internal cavity 725 may be configured to accommodate various internal components in different combinations, providing flexibility in device configuration and user experience customization. A star-shaped cylindrical filter 735 can be positioned within the internal cavity 725 and may feature a star-shaped cross-section as shown in the example of FIG. 7. The star-shaped cross-section can provide multiple channels or grooves that allow airflow while maximizing surface area contact with the passing air. Alternative cross-sectional configurations for the cylindrical filter 735 can include circular, oval, triangular, hexagonal, or other polygonal shapes depending on the desired airflow characteristics and manufacturing considerations. In an example where a non-porous material is used for the filter 735, a cross-sectional shape with more apertures or voids can be selected to allow sufficient airflow. If the material selected is porous, the filter 735 can have few, smaller, or no apertures or voids.

The sensation insert 750 can be positioned within the internal cavity 725 and may include an aperture running through its longitudinal center to allow controlled airflow. The aperture can be sized to provide a specific level of air resistance while ensuring adequate airflow for user inhalation. In alternative embodiments, the sensation insert 750 can be constructed from porous material that allows airflow through the material itself rather than through discrete apertures. The porous material can include cotton, foam, or other permeable materials with varying densities to achieve different airflow characteristics.

Air restrictors 745 and 755 can be positioned within the internal cavity 725 to provide additional control over airflow resistance and air distribution. The air restrictors 745 and 755 can include multiple apertures arranged in various patterns to optimize airflow characteristics. The aperture patterns can include a central aperture surrounded by multiple smaller apertures, concentric rings of apertures, or asymmetrical patterns designed to create specific airflow dynamics. The size and number of apertures in the air restrictors 745 and 755 can be varied to accommodate different user preferences and to compensate for changes in sensation intensity as the device ages. In some examples, such as the example of FIG. 7, the air restrictors 745, 755 have no apertures at all and instead restrict flow based on the porosity of the material selected.

The modular design allows the internal components 735, 745, 750, and 755 to be used individually or in any combination within the internal cavity 725. A user can select specific combinations of components to achieve desired airflow resistance, sensation intensity, and overall inhalation experience. For example, the device 710 can be configured with only the sensation insert 750 for minimal airflow restriction, or can include multiple air restrictors 745 and 755 along with the star-shaped cylindrical filter 735 for maximum airflow control and sensation delivery.

The interchangeable nature of the internal components allows users to modify the device configuration as needed. Components can be removed and replaced to adjust airflow characteristics, change sensation profiles, or refresh components that have lost effectiveness over time. The internal cavity 725 can be dimensioned to accommodate the various component combinations while maintaining proper sealing and airflow continuity throughout the device 710.

The flavor solutions used to infuse the permeable tube can encompass a wide range of taste profiles to accommodate diverse user preferences. Non-menthol and non-spice flavor options can provide users with familiar and appealing taste experiences without additional cooling or warming sensations. Chocolate cream flavor solutions can be formulated using cocoa extracts and vanilla compounds to create a rich, dessert-like taste profile that users experience when their lips contact the outer surface of the permeable tube. Peppermint flavor solutions can incorporate natural peppermint oils and extracts to deliver a fresh, minty taste without the cooling sensation typically associated with menthol compounds.

Wintergreen flavor solutions can utilize methyl salicylate and related compounds to provide the characteristic wintergreen taste that many users find refreshing and familiar. Mixed berry flavor solutions can combine extracts from strawberries, blueberries, raspberries, and blackberries to create a complex fruit profile that delivers multiple taste notes during inhalation. Fruit punch flavor solutions can blend various tropical and citrus fruit extracts to produce a sweet, fruity taste reminiscent of traditional fruit punch beverages.

Strawberry vanilla flavor combinations can incorporate natural strawberry extracts with vanilla compounds to create a creamy, dessert-inspired taste profile. Toasted or salted caramel flavor solutions can utilize caramelized sugar compounds combined with salt extracts to deliver a sophisticated, sweet-savory taste experience. Sour apple flavor solutions can incorporate malic acid and apple extracts to provide a tart, fruity taste that appeals to users who prefer more acidic flavor profiles.

Virginia blend flavor solutions can utilize tobacco leaf extracts and sweetening compounds to create a sweet tobacco taste without the harmful combustion products associated with traditional tobacco use. Cotton candy flavor solutions can incorporate ethyl maltol and vanilla compounds to recreate the distinctive spun sugar taste of carnival cotton candy. Cucumber flavor solutions can utilize fresh cucumber extracts to provide a clean, refreshing taste that many users find cooling and pleasant.

Menthol-enhanced flavor solutions can combine the base flavors described above with menthol compounds to create cooling sensations that complement the primary taste profiles. Watermelon ice flavor solutions can blend watermelon extracts with menthol compounds to deliver both the sweet, fruity taste of watermelon and a cooling throat sensation. Cucumber ice flavor solutions can enhance the natural cucumber taste with menthol to create an intensely refreshing experience that combines the clean cucumber flavor with cooling properties.

Raspberry ice flavor solutions can incorporate raspberry extracts with menthol compounds to provide the tart-sweet taste of raspberries enhanced by cooling sensations. Grape ice flavor solutions can combine grape extracts with menthol to deliver the familiar grape taste with added cooling effects. Mixed berry ice flavor solutions can enhance the complex berry taste profile with menthol compounds to create a cooling fruit experience.

Fruit punch ice flavor solutions can add menthol compounds to the tropical fruit blend to create a refreshing, cooling version of the traditional fruit punch taste. Sour apple ice flavor solutions can combine the tart apple taste with menthol compounds to provide both the acidic fruit flavor and cooling throat sensations that many users find particularly satisfying.

The concentration of flavor compounds in these solutions can be adjusted to achieve different intensity levels, allowing manufacturers to create mild, medium, or strong flavor variants of each profile. The flavor solutions can be formulated using food-grade ingredients and natural extracts to ensure safety and palatability. The permeable tube material can be selected based on its ability to absorb and retain these various flavor solutions while maintaining structural integrity and allowing proper airflow through the device.

The example device of FIG. 7 can be configured by users through various methods to achieve desired flow characteristics, flow restriction levels, and flavor profiles. Users can manipulate the modular internal components 735, 745, 750, and 755 within the internal cavity 725 to customize their inhalation experience according to personal preferences and changing needs over time.

A user can configure the device 710 for minimal flow restriction by inserting only the sensation insert 750 into the internal cavity 725. This configuration can provide the most open airflow path while still delivering sensation from the essential oils or extracts infused within the sensation insert 750. The single aperture through the longitudinal center of the sensation insert 750 can allow relatively unrestricted airflow, making this configuration suitable for users who prefer easier inhalation with moderate sensation delivery.

For increased flow restriction and enhanced sensation delivery, a user can combine the sensation insert 750 with one or both air restrictors 745 and 755. The air restrictors 745 and 755 can be positioned on either side of the sensation insert 750 within the internal cavity 725 to create additional resistance points in the airflow path. This configuration can alter the airflow through the sensation insert 750, potentially increasing the extraction of sensation compounds and delivering a more intense experience to the user.

Users can achieve maximum flow control and sensation intensity by utilizing all available internal components 735, 745, 750, and 755 within the internal cavity 725. The star-shaped cylindrical filter 735 can be positioned to maximize surface area contact with the airflow, while the air restrictors 745 and 755 can provide precise flow control at multiple points along the airflow path. This full configuration can create the highest level of air resistance while maximizing the contact between airflow and sensation-infused surfaces.

The modular design allows users to experiment with different component arrangements to find their preferred configuration. A user can position the star-shaped cylindrical filter 735 at different locations within the internal cavity 725 to alter the airflow dynamics and sensation delivery characteristics. The star-shaped cross-section of the cylindrical filter 735 can create multiple airflow channels that can be optimized based on the filter's position relative to other components.

Users can replace individual components as the device ages and sensation intensity diminishes over time. When the sensation insert 750 begins to lose effectiveness, a user can remove it from the internal cavity 725 and replace it with a fresh insert soaked in sensation solution. Similarly, air restrictors 745 and 755 can be swapped with alternatives having different aperture patterns or sizes to compensate for reduced sensation delivery from aging components.

The aperture patterns in the air restrictors 745 and 755 can be selected by users to achieve specific airflow characteristics. Air restrictors with larger central apertures and fewer surrounding holes can provide lower resistance with concentrated airflow, while restrictors with multiple small apertures can create higher resistance with distributed airflow patterns. Users can test different restrictor combinations to determine which aperture configurations best suit their inhalation preferences.

Users can configure the device 710 to accommodate seasonal preferences or changing taste requirements by selecting different combinations of internal components. During periods when stronger sensation delivery may be desired, users can configure the device with multiple air restrictors and the star-shaped cylindrical filter 735 to maximize air-to-material contact. When milder sensations may be preferred, users can remove some components to reduce flow restriction and sensation intensity.

The sensation insert 750 can be replaced with inserts soaked in different sensation solutions to provide variety in the user experience. A user can maintain multiple sensation inserts infused with different essential oils or extracts, allowing them to change the sensation profile of the device 710 without replacing the entire unit. This interchangeability can enable users to experiment with different sensation combinations or to match their preferences to different times of day or activities.

Users can adjust the overall flow resistance of the device 710 by varying the number and positioning of air restrictors 745 and 755 within the internal cavity 725. A single air restrictor can provide moderate flow control, while multiple restrictors positioned at different points can create graduated resistance that affects both the inhalation effort required and the sensation delivery characteristics. The spacing between restrictors can also influence the airflow dynamics and user experience.

The star-shaped cylindrical filter 735 can be oriented in different rotational positions within the internal cavity 725 to alter the alignment of its grooves with the airflow path. Users can experiment with different orientational configurations to optimize the interaction between the star-shaped channels and the overall airflow pattern through the device 710. This rotational adjustment can provide fine-tuning capabilities for users seeking to optimize their inhalation experience.

Users can configure the device 710 for different usage scenarios by selecting appropriate component combinations. For extended use sessions, a configuration with higher flow restriction can help preserve sensation compounds by reducing the rate at which they are depleted from the inserts. For shorter, more intense sessions, a more open configuration can provide immediate sensation delivery with less inhalation effort required from the user.

The modular configuration allows users to maintain consistent performance as individual components wear or lose effectiveness. When the star-shaped cylindrical filter 735 becomes less effective due to accumulated residue or material degradation, users can replace it while retaining other components that may still be functioning optimally. This selective replacement capability can extend the overall service life of the device 710 while maintaining desired performance characteristics.

Additional examples of the multiple-sensation inhalation device can incorporate alternative materials and construction methods that provide enhanced durability and manufacturing efficiency. An example device can utilize a ceramic tube instead of bamboo, where the ceramic material may be porous enough to absorb and retain flavor solutions while providing resistance to moisture and temperature variations. The ceramic tube can be formed through slip casting or pressing techniques that create the desired porosity characteristics for flavor absorption.

An example manufacturing method can include injection molding of thermoplastic materials to create the permeable tube structure. The thermoplastic material can be formulated with controlled porosity through the incorporation of water-soluble additives that are subsequently removed during processing. This approach can provide consistent porosity throughout the tube wall while enabling mass production techniques that reduce manufacturing costs.

Alternative sensation delivery methods can include the use of encapsulated essential oils within the cotton inserts. The encapsulation can utilize biodegradable polymer shells that release sensation compounds gradually during use, extending the effective life of the sensation insert. The encapsulated oils can be distributed throughout the cotton material during the soaking process, providing more uniform sensation delivery compared to conventional liquid soaking methods.

An example device configuration can incorporate multiple chambers within the internal cavity 725 to separate different sensation solutions. The chambers can be formed by internal dividers or separate compartments that allow users to experience sequential sensations during a single inhalation cycle. The first chamber can contain cooling sensations while the second chamber can provide warming or tingling sensations, creating a complex sensory experience.

Temperature-activated sensation compounds can be incorporated into the sensation solutions to provide enhanced user experiences. These compounds can remain dormant at room temperature but activate when exposed to the warmth of the user's breath during inhalation. The temperature activation can provide more intense sensations that correspond directly to the user's inhalation activity.

An example method can include the use of ultrasonic welding to join multiple tube sections together, creating devices with different material properties in different sections. The mouthpiece section can be constructed from flavor-absorbing materials while the body section can be made from materials optimized for structural integrity. The ultrasonic welding process can create hermetic seals between sections while maintaining the internal cavity dimensions required for proper component fit.

Alternative insert materials can include natural sponge materials that provide different absorption and release characteristics compared to cotton. Sea sponge materials can offer retention of sensation solutions while providing unique texture interactions with airflow. The natural pore structure of sponge materials can create different airflow patterns that enhance sensation delivery through increased turbulence and mixing.

An example device can incorporate replaceable flavor cartridges that attach to the exterior of the permeable tube. The flavor cartridges can contain concentrated flavor solutions that gradually migrate through the tube wall during use. This configuration can allow users to change flavor profiles without replacing the entire tube structure, extending the useful life of the device while providing flavor variety.

Magnetic coupling systems can be incorporated into example devices to facilitate easy assembly and disassembly of internal components. Magnetic inserts can be embedded within the cotton inserts and corresponding magnetic elements can be positioned within the tube structure. This magnetic coupling can ensure proper positioning of inserts while allowing easy removal for replacement or cleaning.

An example manufacturing process can include 3D printing of the tube structure using materials that incorporate flavor compounds directly into the printing filament. The 3D printing process can create complex internal geometries that optimize airflow patterns while embedding flavor compounds throughout the tube wall. This approach can eliminate the separate soaking step while providing more uniform flavor distribution.

Alternative airflow control methods can include adjustable external vents that allow users to modify air intake characteristics during use. The external vents can be positioned along the tube length and can include sliding covers or rotating sleeves that change the effective vent area. This external control can provide real-time adjustment of airflow resistance without requiring internal component changes.

An example device can incorporate biodegradable materials throughout its construction to address environmental concerns. The tube structure can be formed from plant-based polymers that decompose naturally after disposal. The cotton inserts can be replaced with hemp or other natural fiber materials that provide similar absorption characteristics while offering improved biodegradability.

Alternative tube geometries can include tapered designs that create variable airflow velocities along the tube length. The tapered geometry can accelerate airflow through sensation-rich regions while providing comfortable mouthpiece dimensions. The velocity changes can enhance the extraction of sensation compounds from inserts while maintaining user comfort during inhalation.

An example manufacturing method can include laser perforation of the cotton inserts to create precise aperture patterns with controlled dimensions. The laser perforation process can create apertures with smooth edges and consistent diameters that optimize airflow characteristics. The laser process can also create complex aperture patterns that would be difficult to achieve through conventional mechanical perforation methods.

Alternative coupling mechanisms can include threaded connections between the tube sections and removable end caps. The threaded connections can provide secure assembly while allowing easy disassembly for component replacement or cleaning. The threads can be designed with fine pitch to provide precise adjustment of internal component compression and positioning.

An example device can incorporate antimicrobial coatings on internal surfaces to prevent bacterial growth during extended use periods. The antimicrobial coatings can utilize silver nanoparticles or other proven antimicrobial agents that remain effective throughout the device lifetime. These coatings can be applied through vapor deposition or spray coating processes that provide uniform coverage of complex internal geometries.

Pressure-sensitive adhesive systems can be incorporated into example devices to provide temporary attachment of external accessories or identification labels. The pressure-sensitive adhesives can be formulated to provide strong initial adhesion while allowing clean removal without residue. This capability can enable users to customize their devices with personal identification or decorative elements.

Other examples of the disclosure will be apparent to those skilled in the art from consideration of the specification and practice of the examples disclosed herein. Though some of the described methods have been presented as a series of steps, it should be appreciated that one or more steps can occur simultaneously, in an overlapping fashion, or in a different order. The order of steps presented are only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the disclosure being indicated by the following claims.

What is claimed is:

1. A method for providing a multiple-sensation inhalation device, comprising:
- machining a permeable tube to include a hollow cavity having an inlet and an outlet;
- soaking the permeable tube in a flavor solution such that the flavor solution penetrates the permeable tube;
- providing a first insert shaped to fit within the inlet of the permeable tube and having at least one aperture allowing air flow through the first insert;
- soaking the first insert in a sensation solution having at least one essential oil or extract;
- inserting the first insert into the inlet of the permeable tube; and
- inserting a second insert into the inlet of the permeable tube, wherein the second insert includes multiple apertures that allow air to flow through the second insert.

2. The method of claim 1, wherein the flavor solution includes at least one of bubble gum, fruit, tiramisu, or chocolate flavor.

3. The method of claim 1, wherein the sensation solution includes at least one of peppermint, menthol, lavender, vitamin B12, caffeine, nicotine, THC, CBD, or betel nut.

4. The method of claim 1, wherein the permeable tube retains the flavor solution such that a user experiences a taste when inhaling through the permeable tube, based on the user's lips contacting an outer surface of the permeable tube.

5. The method of claim 1, wherein the first insert retains the sensation solution such that a user experiences a corresponding sensation when inhaling through the first insert.

6. The method of claim 1, wherein the multiple apertures are arranged in a pattern having a central aperture and multiple apertures surrounding the central aperture.

7. A multiple-sensation inhalation device, comprising:
- a permeable tube that includes:
  - a body portion having a hollow cavity with an inlet and an outlet, wherein the body portion is infused with a flavor solution;
  - a first insert within the hollow cavity, wherein the first insert is:
    - infused with a sensation solution having at least one essential oil or extract; and
    - perforated with at least one passage to allow airflow through the first insert; and
  - a second insert within the hollow cavity, wherein the second insert includes multiple apertures that allow air to flow through the second insert.

8. The multiple-sensation inhalation device of claim 7, wherein the flavor solution includes at least one of bubble gum, fruit, tiramisu, or chocolate flavor.

9. The multiple-sensation inhalation device of claim 7, wherein the sensation solution includes at least one of peppermint, menthol, lavender, vitamin B12, caffeine, nicotine, THC, CBD, or betel nut.

10. The multiple-sensation inhalation device of claim 7, wherein the body portion retains the flavor solution such that a user experiences a taste when inhaling through the permeable tube, based on the user's lips contacting an outer surface of the permeable tube.

11. The multiple-sensation inhalation device of claim 7, wherein the first insert retains the sensation solution such that a user experiences a corresponding sensation when inhaling through the first insert.

12. The multiple-sensation inhalation device of claim 7, wherein the multiple apertures of the second insert are arranged in a pattern having a central aperture and a plurality of apertures surrounding the central aperture.

13. A method for providing a multiple-sensation inhalation device, comprising:
- providing a permeable mouthpiece shaped to allow air to flow through the mouthpiece;
- soaking the permeable mouthpiece in a flavor solution such that the flavor solution penetrates the permeable mouthpiece;
- coupling the permeable mouthpiece to a tube such that air can flow through the combined tube and mouthpiece;
- soaking a first insert in a sensation solution having at least one essential oil or extract;
- inserting the first insert into the tube; and
- inserting a second insert into the tube, wherein the second insert includes multiple apertures that allow air to flow through the second insert.

14. The method of claim 13, wherein the multiple apertures of the second insert are arranged in a pattern having a central aperture and a plurality of apertures surrounding the central aperture.

15. A method for providing a multiple-sensation inhalation device, comprising:
- providing a permeable tube shaped to allow air to flow through the permeable tube and including a proximal end and a distal end;

soaking the proximal end of the permeable tube in a flavor solution such that the flavor solution penetrates the proximal end of the permeable tube;

soaking the distal end of the permeable tube in a sensation solution such that the sensation solution penetrates the distal end of the permeable tube; and inserting an air resistance insert into the permeable tube to provide resistance to a user when inhaling.

16. The method of claim 15, wherein the air resistance insert is soaked in the sensation solution prior to insertion.

17. The method of claim 15, wherein the air resistance insert is replaceable by a user.

* * * * *